United States Patent [19]

Freudenberger et al.

[11] 4,214,106
[45] Jul. 22, 1980

[54] PROCESS FOR THE PREPARATION OF ETHYLENE GLYCOL

[75] Inventors: Dieter Freudenberger, Hofheim am Taunus; Friedrich Wunder, Flörsheim am Main, both of Fed. Rep. of Germany

[73] Assignee: Hoechst Aktiengesellschaft, Frankfurt, Fed. Rep. of Germany

[21] Appl. No.: 893,823

[22] Filed: Apr. 5, 1978

[30] Foreign Application Priority Data

Apr. 7, 1977 [DE] Fed. Rep. of Germany ....... 2715666

[51] Int. Cl.² ............................................. C07C 31/20
[52] U.S. Cl. ................................. 568/864; 252/457; 252/460
[58] Field of Search .......................................... 568/864

[56] References Cited

U.S. PATENT DOCUMENTS

| 2,094,611 | 10/1937 | Lazier | 568/864 |
| 2,285,448 | 6/1942 | Loder | 568/864 |
| 3,478,112 | 11/1969 | Adam et al. | 568/864 |
| 4,088,682 | 5/1978 | Jordan | 568/864 |

FOREIGN PATENT DOCUMENTS

| 2434991 | 2/1976 | Fed. Rep. of Germany | 568/864 |
| 2501499 | 7/1976 | Fed. Rep. of Germany | 568/864 |
| 921477 | 3/1963 | United Kingdom | 568/864 |

Primary Examiner—Joseph E. Evans
Attorney, Agent, or Firm—Curtis, Morris & Safford

[57] ABSTRACT

Process for the preparation of ethylene glycol by hydrogenating glycolic acid in the presence of catalysts containing elements or compounds of elements from at least two of the groups VIII, VIIb and Ib of the Periodic System.

12 Claims, No Drawings

PROCESS FOR THE PREPARATION OF ETHYLENE GLYCOL

The present invention relates to a process for the preparation of ethylene glycol.

The subject of the invention is a one-step catalytic process for the preparation of ethylene glycol from glycolic acid. Ethylene glycol serves, for example, as starting product for the preparation of polyester fibers. In this process, glycol is reacted with terephthalic acid to give polyethylene terephthalate.

Processes for the preparation of ethylene glycol have already been described. In particular the preparation of ethylene glycol from glycolic acid has already been described. A typical feature of the majority of these former processes consists in the fact that the glycolic acid is either esterified first and the ester is then hydrogenolyzed, or the glycolic acid is hydrogenolyzed in admixture with alcohols. This means that not glycolic acid itself, but its esters—where formed in situ—or the polyglycolides being formed in situ as by-products are subjected as the virtual starting products to a hydrogenolysis in order to give the diol. This method (which has in principle already been known from other acids) for the conversion of unsubstituted or substituted carboxylic acids into an alcohol is complicated and burdened by the alcohols which are merely required for the esterification of the glycolic acid and is also very uneconomical, since this esterification shows a strong tendency towards the forming of by-products (etherification, formation of polymers).

In some other publications there has been described also the direct hydrogenolysis of glycolic acid with ruthenium catalysts. This process has the drawback, however, that acceptable yields (of a maximum of 83%) can only be achieved with very high pressures (from 700 to 800 atm.), which makes the technical realization of these processes very difficult. Lower pressures (from 55 to 78 atm.) result in much lower yields (40%).

Other catalysts, especially those on the basis of palladium and platinum, have been described as being completely ineffective, even under reaction conditions which are far more drastic than those required for ruthenium catalysts.

The present invention provides a process for the preparation of ethylene glycol from glycolic acid, which comprises reacting glycolic acid and hydrogen in the presence of a hydrogenation catalyst which contains either (1) a platinum metal of group VIII and/or one of its compounds in admixture with an element of group VIIb and/or one of its compounds, or
(2) a platinum metal of group VIII and/or one of its compounds in admixture with an element of group Ib and/or one of its compounds, or
(3) an element of group VIIb and/or one of its compounds in admixture with an element of group Ib and/or one of its compounds, or
(4) a platinum metal of group VIII and/or one of its compounds in admixture with an element of group VIIb and/or one of its compounds as well as with an element of group Ib and/or one of its compounds.

By "platinum metals of group VIII" there are to be understood the elements ruthenium, rhodium, palladium, osmium, iridium, and platinum. Group VIIb consists of the elements manganese, technetium and rhenium. Group Ib contains the elements copper, silver and gold.

It was a surprising fact which could not have been foreseen that excellent yields are obtained with nearly quantitative conversions even with the catalysts on the basis of palladium and platinum, which had formerly been designated as ineffective. Besides, it has been surprising that in the process of the invention a marked reduction of the reaction pressure is possible in comparison with the former processes, which is also observed even with ruthenium-containing catalysts—again with a very good output.

The process is particularly marked by the fact that it yields practically no by-products. Practically no ethylene glycol is hydrogenated, in spite of the excellent hydrogenation activity of the catalysts, to form liquid or gaseous by-products, such as ethanol or ethane.

Thus, the invention yields a technically simple novel process which can be applied in a very selective manner and which is very economical for the production of ethylene glycol.

The catalysts used in the process according to the invention contain elements or compounds of elements of at least two of groups VIII', VIIb and Ib of the Periodic System in each case (group VIII'=group VIII except for iron, cobalt, nickel), including mixtures of elements or one group with compounds of elements of the other group or groups. There are suitable, above all, manganese, rhenium, ruthenium, rhodium, palladium, osmium, iridium, platinum, gold and silver, or compounds thereof. Preference is given in particular to palladium, platinum, ruthenium, rhenium, gold and silver and the compounds thereof. As combinations there are suitable, above all: Palladium/rhenium, palladium/silver, ruthenium/rhenium, palladium/gold, rhenium/silver, platinum/rhenium, as well as palladium/rhenium/silver, all of these optionally being used as elements and/or compounds.

Surprisingly, a simple combination of elements of group VIIb or their compounds with elements of group Ib or their compounds and/or with platinum metals of group VIII or their compounds results in a selectivity in the formation of ethylene glycol, as it is not achieved with the elements of one group alone or their compounds, especially with silver or rhenium individually, but also with palladium, platinum or ruthenium individually, under such mild reaction conditions.

Besides, it could not have been expected that practically quantitative conversions of glycolic acid are achieved, without a marked reduction of the activity of the catalysts with a prolonged continuous operation or repeated use. The combination of the elements according to the invention has therefore also a highly stabilizing effect and extends the service life of the catalysts, especially when compared with the pure ruthenium catalysts described in the older litereature.

This is of decisive importance for the continuous operation in industry and also implies the superiority of the novel process as compared with the former ones. Besides glycolic acid, other substituted or unsubstituted carboxylic acids may also be hydrogenated with the described catalysts; these are, for example, acetoxyacetic acid, adipic acid, trifluoroacetic acid, pivalic acid and also aromatic carboxylic acids, such as terephthalic acid and naphthalic acid.

The catalysts are generally used in a pulverulent form for the process of the invention. However, they may also be employed in the form of tablets or in admixture with inert materials that may serve as carriers.

As carriers there may be mentioned, for example: silicon dioxide, kieselguhr, titanium dioxide, silicon dioxide-aluminum oxide, charcoal, thorium oxide, zirconium oxide, silicon carbide, spinels, aluminum oxide, magnesium silicate, magnesium silicoacetate, and other silicoacetates. There are suitable especially the silicoacetates or bivalent metals, such as strontium, zinc, cadmium, manganese, cobalt and nickel silico-acetates, either in a pure form or in admixture with silicic acid.

The carriers may be present in a pulverulent form or may be shaped, for example, as granules, pellets, tablets, extruded pieces, saddles, rings or honeycomb tubes.

In case use is made of catalysts supported or admixed with inert materials, the amount of the catalytically active substances is generally in the range of from 0.1 to 50% by weight of the total mass of the catalyst. The amount of the inert materials (carriers) is thus generally in the range of from 99.9 to 50% of the total mass of the catalyst.

The ratio of the elements of group VIII to those of group VIIb and/or group Ib is between 99.9:0.1 and 0.1:99.9, preferably between 10:1 and 1:10.

The catalysts may be present in the form of elements as well as compounds or as mixtures of both. Accordingly, the preparation of the catalysts is effected such that either appropriate compounds are used directly, or these compounds are reduced to a greater or smaller extent, optionally up to the elements.

As compounds there may be mentioned, for example: the oxides, oxide-hydrates, carbonates, nitrates, borides, carboxylates (such as acetates, propionates, butyrates), chelates of 1,3-diketo compounds (for example enolates, such as acetylacetonates, benzoylacetonates, acetylacetic acid ester compounds). Particularly suitable compounds are the carboxylates, acetylacetonates, oxides and oxide-hydrates. For technical and economical reasons the use of, for example, rhenium as potassium perrhenate or rhenium heptoxide and the use of, for example, palladium as palladium-(II)-acetate or -acetylacetonate is particularly preferred, since these products are commercially available. Gold is generally applied onto the carriers as potassium, magnesium or barium acetoaurate.

In order to prepare, for example, palladium-rhenium catalysts, a solution of a palladium carboxylate or of a compound being converted with carboxylic acids into palladium carboxylate, such as palladium oxide hydrate, palladium nitrate, palladium oxycarbonate or of a salt of a 1,3-diketo compound, such as acetylacetic acid ester or acetyl acetone, is generally applied onto the carrier in an anhydrous or aqueous carboxylic acid, together with perrhenium acid or its salts, by way of impregnating, dipping or suspending the carrier, or by spraying. The carboxylic acid is then eliminated by drying at elevated temperatures in vacuo or at normal pressure. The catalyst may then be used directly. However, it is preferably treated with reducing agents in the gaseous or liquid phase at a temperature in the range of from 15° to 200° C.

As carboxylic acid there may be used all liquid aliphatic carboxylic acids having from 2 to 10 carbon atoms which are vaporizable in vacuo without decomposition. Preference is given to acetic acid, propionic acid and butyric acid, but especially acetic acid.

For the preparation of one of the catalysts claimed according to the invention there are also suitable solutions in acetone, $CH_2Cl_2$, methanol, or acetone/water.

The solutions of the compounds used for the preparation of the catalysts may be applied separately onto the carriers. However, it is advantageous to dissolve them together in an appropriate solvent.

It is for example also possible, however, to apply first one of the palladium compounds mentioned above onto the carrier and to apply thereafter the solution of the second or third catalyst component, for example, a rhenium compound.

If a reduction of said component is desired, it can be effected in the liquid phase, for example with hydrazine hydrate. However, it is advantageous to effect the reduction at higher temperatures, for example temperatures in the range of from 100° to 200° C. in the gaseous phase with reducing gases, such as hydrogen, methanol, formaldehyde, ethylene, propylene, butenes. A strong dilution of the reducing gases with inert gases, such as nitrogen, carbon dioxide or noble gases, in the starting period of the reduction and an increase of the concentration of the reducing agent performed with a progressive reduction has proved to be particularly advantageous, so that the reduction is completed, for example, in pure hydrogen. The reduction may be effected in a separate device as well as in the same apparatus which is used in the conversion of glycolic acid to give ethylene glycol.

The catalysts may sometimes be pyrophorous; in this case they must be treated accordingly. Especially in these cases a reduction of the catalyst and the subsequent reaction of glycolic acid in one and the same apparatus is advantageous. However, generally the catalysts are surprisingly stable towards oxygen or oxygen-containing gases (air), particularly if they have been applied onto silicoacetate carriers.

For the operation in industry, it is also an important factor in the one-step process of the invention for the preparation of ethylene glycol from glycolic acid that practically no by-products are formed, such as polyglycol ether, which would make further processing difficult and would strongly increase the costs.

In order to achieve an optimum performance regarding the process according to the invention, elevated pressures and temperatures are generally applied.

The reaction temperatures are generally in the range of from 50° to 300° C., preferably from 130° to 250° C. The reaction pressure is generally between 50 and 500 bars. Preferably a range of from 100 to 350 bars is applied.

The hydrogen used for the hydrogenolysis of glycolic acid is generally used in a greater stoichiometric excess. Unreacted hydrogen may be recycled into the reaction. The hydrogen is generally used in a technically pure form. However, additions of inert gases, for example nitrogen, do not disturb the reaction.

The reaction may be carried out continuously as well as discontinuously.

The reaction time for the process of the invention is generally in the range of from 5 minutes to 8 hours. For example, it is from about 1 to 6 hours, if the process is carried out discontinuously in the autoclave.

Pulverulent catalyst may be filtered off or eliminated by centrifuging upon completion of the test and may thus be used again, without noticeable losses in activity.

In the continuous operation, for example in the flooded reactor or in the trickling phase, use is generally made of tabletted catalysts or of those supported on carriers. For this purpose, granulated carbon or a granulated magnesium silicate which has been partially freed from mangesium by means of acetic acid (magnesium silicoacetate) have proved to be particularly advantageous.

However, also silicoacetates of other elements, preferably bivalent elements, are particular suitable as carriers in these cases.

An appropriate carrier is obtained, for example, in the following manner:

A commercial magnesium silicate, for example a mineral having the following composition

| 56 to 60% of $SiO_2$ | 1% of $Na_2O$ + $K_2O$ |
|---|---|
| 22 to 22.5% of MgO | 0.5% to 1.3% of $Fe_2O_3$ |
| 1.2 to 3.5% of $Al_2O_3$ | 0.2% of $TiO_2$ |
| 1.9 to 4.3% of CaO | 2.5% of $CO_2$ | is treated with acetic acid. A catalyst carrier is obtained, whose composition was analyzed to be the following:

68.5% of $SiO_2$
14% of MgO
13.4% of $CH_3COOH$ (calculated as acetate)
3.6% of $Al_2O_3$
0.5% of $Fe_2O_3$ and whose pore volume is in the range of from b 0.7 to 1.2 ml/g and the apparent density of which is from 0.4 to 0.69 g/ml.

In a corresponding manner, the corresponding silicoacetates can also be prepared from other natural or synthetic silicates.

Particularly suitable, besides magnesium silicate, is synthetic calcium silicate which is commercially available. Instead of acetic acid there may also be used acetic acid/water, acetic acid/methanol or acetic acid/acetone.

In the practical execution of the hydrogenolysis, the solvents known for hydrogenation processes, such as dioxan, tetrahydrofuran or other cyclic or open-chain ethers, for example tetrahydropyrane or diethyl ether, may be used. There may also be employed polyalkylene-glycol dialkyl ethers, for example tetramethylene-glycol dibutyl ether, tetramethylene-glycol dipentyl ether, tetraethylene-glycol dimethyl ether, tetraethylene-glycol diethyl ether and diethylene-glycol dibutyl ether, or mixtures of these solvents. Especially dioxan and tetrahydrofuran have proved to be appropriate, but also other solvents, such as water, are suitable.

The content of glycolic acid in the starting solution is generally in the range of from 5 to 60%. Particularly suitable has been, for example, the use of glycolic acid as a 10 to 40% solution in 1,4-dioxan or THF. The amount of catalyst required for the hydrogenation is generally in the range of from 0.5 to 40% of the amount of glycolic acid or from about 0.2 to 25%, calculated on the total mixture (glycolic acid and solvent), if the process is carried out discontinuously. Glycolic acid may also be used without solvent, however.

The working-up of the reaction mixtures is generally effected by fractionated distillation.

Of the various operating methods, the following one has proved to be particularly advantageous in the discontinuous preparation of ethylene-glycol:

A solution of glycolic acid in 1,4-dioxan is introduced, together with the catalyst, into a high-pressure autoclave, thereafter hydrogen is added, and the reaction mixture is heated. Upon completion of the reaction the mixture is cooled, the catalyst is separated, and the mixture is subjected to fractionated distillation.

The following Examples serve to illustrate the process of the invention.

EXAMPLE 1

30 Grams of palladium-(II) acetate and 4 g of rhenium heptoxide are dissolved in 600 ml of glacial acetic acid, and 100 g kieselguhr (pure, washed with hydrochloric acid) are added. The catalyst is dried in the water jet vacuum in a rotary evaporator at 60° C., is then slowly heated under normal pressure to 200° C. in a nitrogen current and reduced for 4 hours with 5% of hydrogen in the nitrogen. The cooling is effected under a nitrogen atmosphere.

0.2 Mole of glycolic acid (15.2 g) are dissolved in 100 ml of dioxan (103 g). The solution is introduced, together with 5 g of the catalyst which contains 10.6% of palladium and 2.3% or rhenium, into a 1 liter high-pressure shaking autoclave. Upon closing the autoclave, hydrogen is added, until the internal pressure has reached 200 bars, then the shaking device is operated, and the mixture is heated to 172° C. within 45 minutes. After about 6 hours the reaction is interrupted, and the mixture is cooled. Upon separating the catalyst, 116.3 g of a water-clear colorless reaction solution is obtained, which contains 9.9% (11.61 g) of ethylene glycol, which corresponds to a yield of 93.6% of the theory. Besides glycol and the solvent dioxan, water and a small amount of ethanol (0.3 g) can be detected. The starting material (glycolic acid) is no longer present.

EXAMPLE 2

15.2 Grams of glycolic acid are dissolved in 100 ml of dioxan. The solution is reacted together with 5.3 g of the catalyst which has already been used in Example 1, has been filtered off and still contains a small amount of moisture, as has been described in Example 1.

115.8 Grams of a solution which is again colorless and clear as water are obtained, the solution containing 9.7% (11.23 g) of ethylene glycol, which corresponds to 90.5% of the theoretical yield.

EXAMPLE 3

A natural magnesium silicate having a grain size of from 3 to 4 mm is boiled with 50% acetic acid, until magnesium ions are not dissolved any more. After drying, 500 g of this carrier are impregnated with a solution of 22 g of palladium acetate and 3.1 g of rhenium heptoxide in 400 ml of acetic acid, then dried in the rotary evaporator at 60° C. and in the water jet vacuum and reduced at 200° C. under normal pressure with a mixture of hydrogen and nitrogen (5%, 95%).

0.2 Mole of glycolic acid (15.2 g) are dissolved in 100 ml of dioxan (103 g). The solution is introduced into a 0.5 liter magnetic type lifting shaking autoclave together with 5 g of the granulated catalyst containing 2% of palladium and 0.46% of rhenium.

The autoclave is closed, hydrogen is added, until the pressure is 195 bars, and the mixture is rapidly heated to 165° C., while stirring constantly. After about 5 hours the reaction is discontinued, the mixture is cooled to 20°, and the catalyst is separated from the reaction mixture by filtration.

114 Grams of a clear colorless solution are obtained, which solution contains—according to the gas-chromatographic analysis—9.56% (10.9 g) of ethylene glycol, which corresponds to 87.8% of the theoretical yield.

EXAMPLE 4

In a rotary evaporator, a solution of 15 g of palladium acetate in 400 ml of glacial acid and 5 g of silver nitrate in 80 ml of water is added to 50 g of kieselguhr washed with hydrochloric acid, the mixture is dried at 60° C. in the water jet vacuum and is then reduced at 200° C. under normal pressure with a mixture of hydrogen and nitrogen (5%, 95%).

0.2 Mole of glycolic acid (15.2 g) is dissolved in 112 ml of tetrahydrofuran (100 g). The solution is introduced, together with 4 g of the pulverulent catalyst containing 10% of palladium and 4% of silver, into a 0.5 liter magnetic type lifting shaking autoclave. The contents are purged shortly with hydrogen, and thereafter hydrogen is added, until the pressure is 178 bars. The mixture is then heated to 240° C. within half an hour and is allowed to react for 5½ hours.

After this time the mixture is cooled, and the catalyst is separated by means of a centrifuge. The water-clear reaction solution obtained (108 g) contains 9.3% or 10.44 g of ethylene glycol, which corresponds to a yield of 80.9% of the theory. Besides, small amounts of ethanol (0.1% in the reaction solution) and traces of n-butanol can be detected by way of gas chromatography.

EXAMPLE 5

9.3 Grams of platinum acetate and 2.2 g of rhenium heptoxide are dissolved in 300 ml of glacial acetic acid, thereafter 50 g of washed kieselguhr are added, and the mixture is dried in the rotary evaporator at 60° C. under a water jet vacuum. Subsequently the mixture is reduced at normal pressure and a temperature of 200° C. with a mixture of hydrogen and nitrogen (5%, 95%) for 4 hours and is then allowed to cool under a nitrogen atmosphere.

0.5 Mole of glycolic acid (38.02 g) are dissolved in 100 ml of dioxan (103 g). 5 Grams of the pulverulent catalyst which contains 10% of platinum and 3% of rhenium are added to the solution, and the mixture is hydrogenated (hydrogen pressure 210 bars) at 175° C. in a high pressure shaking autoclave.

After a reaction time of 4½ hours the mixture is rapidly cooled, the catalyst if filtered off and the reaction solution is subjected to an analysis performed by way of gas chromatography. 138.3 Grams of reaction solution are obtained, which contains 20.5% (28.35 g) of ethylene glycol, which corresponds to 91.4% of the theoretical yield.

EXAMPLE 6

4.4 Grams of ruthenium chloride hydrate ($RuCl_3 \cdot x H_2O$) and 0.5 g of rhenium heptoxide are dissolved in 50 ml of water, then 15 g of washed kieselguhr are added, and the mixture is dried in the rotary evaporator. Subsequently the catalyst is heated to 100° C. in a glass tube under 12 Nl of nitrogen per hour. Thereafter a mixture of hydrogen and nitrogen (4:96) is added, and the mixture is heated to 200° C. within 4 hours and is then heated under hydrogen/nitrogen (17:83) to 325° C., and under hydrogen/nitrogen (30:70) to 350° C., whereupon it is reduced for 1 hour under pure hydrogen.

0.5 Mole of glycolic acid (38.02 g) is dissolved in 100 g of tetrahydrofuran. The solution is introduced, together with 2.5 g of the pulverulent catalyst containing 10% of ruthenium and 2.3% of rhenium, into a high-pressure shaking autoclave; thereafter hydrogen is introduced (205 bars), and the mixture is rapidly heated to 215° C.

After a reaction period of 3½ hours, 136 g of a clear reaction solution are obtained which shows a slightly yellowish color shade, and wherein 28.5 g of glycol are contained, which corresponds to 91.9% of the theory.

Besides, the analysis performed by way of gas chromatography shows traces of n-butanol, as well as about 0.2 g of ethanol.

EXAMPLE 7

6 Grams of rhodium acetate and 1 g of rhenium heptoxide are dissolved in 100 ml of acetic acid, 25 g of washed kieselguhr are added, and the mixture is dried in the rotary evaporator at 60° C. in the water jet vacuum. Subsequently said mixture is reduced under normal pressure with 1% of hydrogen in nitrogen at 200° C. for 8 hours.

0.2 Mole of glycolic acid (15.21 g) are introduced, together with 100 ml of dioxan and 1.9 g of the catalyst containing 10% of rhodium and 2.3% of rhenium, into a high-pressure shaking autoclave. Hydrogen is introduced (183 bars), and the mixture is heated to 238° C. After 6 hours the reaction is interrupted, the finely divided catalyst is eliminated by centrifuging, and the solution (112 g) is subjected to an analysis performed by way of gas chromatography. It contains 9.3 g (74.9% of the theory) of ethylene glycol.

EXAMPLE 8

3.6 Grams of palladium acetate, 0.27 g of silver acetate and 0.22 g of rhenium heptoxide are dissolved in 100 ml of acetic acid, 15 g of washed kieselguhr are added, and the mixture is dried in the rotary evaporator at 60° C. under a water jet vacuum. Subsequently the mixture is reduced with a mixture of hydrogen and nitrogen (5%, 95%) under normal pressure and at a temperature which is slowly rising to 200° C.

4.5 Grams of the catalyst containing 10% of palladium, 1% of silver and 1% of rhenium are introduced into a solution of 0.5 mole (38.02 g) of glycolic acid in 90 ml of dioxan and 10 ml of water, and the mixture is introduced into an autoclave provided with a silver lining. Hydrogen is introduced (175 bars) and the mixture is heated to 155° C., while stirring. After a reaction period of 4 hours, 132 g of reaction solution are obtained which contain 28.9 g of ethylene glycol, which corresponds to 93.5% of the theory.

EXAMPLE 9

A magnesium silicate being found in nature and having a grain size of from 3 to 4 mm is boiled with 30% acetic acid, until magnesium acetate ions are not dissolved any more. 500 Grams of this carrier are repeatedly impregnated with a solution of 150 g of palladium acetate and 20 g of rhenium heptoxide in 3 l of acetic acid and dried, until the entire solution has been applied. Subsequently the mixture is reduced with hydrogen/nitrogen (1%, 99%) and at a temperature which is slowly rising to 200° C.

0.2 Mole of glycolic acid (15.21 g) is dissolved in 100 ml of dioxan. To this solution there are added 3 g of the granulated (grain size of from 3 to 4 mm) catalyst which contains 10% of Pd and 2.3% of rhenium, and the mixture is hydrogenated under a hydrogen pressure of 193 bars at 160° C. in a 1 liter shaking autoclave. After a reaction period of 5 hours, 114 g of reaction solution are obtained which contain 11.2 g of ethylene glycol.

EXAMPLE 10

1.5 Grams of silver nitrate and 0.4 g of rhenium heptoxide are dissolved in 50 ml of acetone, then 10 g of washed kieselguhr are added, and the mixture is dried in the rotary evaporator and reduced with a mixture of hydrogen and nitrogen (1%, 99%) at 200° C.

0.2 Mole of glycolic acid is dissolved in 100 g of tetrahydrofuran. To this solution there are added 5 g of the catalyst containing 10% of silver and 2.7% of rhenium, and the mixture is hydrogenated under 210 bars of hydrogen at 228° C. in a high-pressure autoclave.

After a reaction period of 6 hours, 109 g of reaction solution are obtained which contain 8.3 g of ethylene glycol (66.9% of the theory).

EXAMPLE 11

10 Grams of active charcoal granules having a grain size of from 1 to 3 mm are impregnated with a solution of 3 g of ruthenium chloride hydrate and 0.34 g of rhenium heptoxide in 9 ml of water, then dried at 60° C. and reduced with a mixture of 1% of hydrogen and nitrogen (1%, 99%) at a temperature which is slowly rising to 250° C.

0.5 Mole of glycolic acid (38.02 g) is dissolved in a mixture of 80 g of tetrahydrofuran and 20 g of water. To this solution there are added 4.8 g of the granulated catalyst containing 10% of ruthenium and 2.3% of rhenium, thereafter the mixture is introduced into an autoclave provided with a silver lining, hydrogen is added (168 bars), and subsequently the mixture is heated to 158° C. within 45 minutes. After a reaction period of 2 hours the process is interrupted, the mixture is rapidly cooled and is then separated from the catalyst.

134 Grams of reaction solution are obtained, which contain 29.1 g of ethylene glycol (93.8% of the theory).

EXAMPLE 12

3.6 Grams of palladium acetate and 0.044 g of rhenium heptoxide are dissolved in 75 ml of glacial acetic acid, are mixed with 15 g of washed kieselguhr and dried in the rotary evaporator under a water jet vacuum at 60° C. Subsequently the mixture is reduced at normal pressure with a mixture of hydrogen and nitrogen (5:95) at a temperature which is slowly rising to 200° C.

0.2 Mole of glycolic acid (15.21 g) is dissolved in 100 ml of dioxan. To this solution there are added 5 g of the pulverulent catalyst containing 10% of palladium and 0.2% of rhenium, the mixture is thereafter introduced into an autoclave, hydrogen is added (185 bars), and the contents are heated to 220° C. After 2½ hours the reaction is discontinued, and the mixture is filtered off from the catalyst.

107.5 Grams of filtrate are obtained which contain 6.3 g of ethylene glycol (51% of the theory).

EXAMPLE 13

1.85 Grams of palladium acetate, 0.28 g of barium acetoaurate and 0.02 g of rhenium heptoxide are dissolved in 50 ml of glacial acetic acid, then 10 g of washed manganese silicate are added to the mixture which is then dried in the rotary evaporator at 60° C. and in a water jet vacuum. Subsequently the mixture is reduced with a hydrogen/nitrogen mixture (1:99) at a temperature which is slowly rising to 200° C.

0.2 Mole of glycolic acid (15.21 g) is dissolved in 100 g of tetrahydrofuran and hydrogenated in the presence of 1.5 g of the catalyst containing 8% of palladium, 1% of gold and 0.1% of rhenium, in an autoclave at 195° C. under 185 bars of hydrogen. After a reaction period of 1.5 hours and upon filtering off the catalyst, 110.8 g of reaction solution are obtained, which contain 8.8% of ethylene glycol (9.75 g; 78.6% of the theory).

EXAMPLE 14

1000 Milliliters of the catalyst described in Example 9 containing 10% of palladium and 2.3% of rhenium on the granulated silicoacetate carrier (grain size from 3 to 4 mm) are introduced into the middle of a reaction tube of a length of 2 m and an inner diameter of 5 cm.

At the lower end of the reactor, 500 g of a solution containing 152 g of glycolic acid dissolved in tetrahydrofuran are introduced per hour by pumping. At the same time hydrogen is added under a pressure of 340 bars, also at the lower end of the reactor, at a rate of about 1.8 Nm$^3$/h. The contents of the reactor are heated within about 1.5 hours to the reaction temperature of 165° C., and the reaction product as well as excess hydrogen are continuously drawn off at the upper end of the reactor.

After the separation of gas and liquid reaction product in a separator being under apparatus pressure, the reaction mixture is collected and analyzed.

About 485 to 520 g of reaction solution are obtained per hour which contain from about 100 to 105 g of glycol (from 80 to 85% of the theoretical yield). After an operation period of about 300 hours, the catalyst still showed the same activity. Palladium and rhenium could not be detected in the amounts discharged.

EXAMPLE 15

A commercial calcium silicate in the form of a powder is mixed with 2% of kaolin, pelleted and calcined at 800° C. These pellets are boiled with 30% acetic acid, until calcium ions are not dissolved any more, and are comminuted after drying to a grain size of from 2 to 3 mm. 10 Grams of this carrier are impregnated with a solution of 0.7 g of palladium acetate and 0.08 g of rhenium heptoxide in 8 ml of glacial acetic acid and are then dried and reduced, as has been described in Example 1.

2 Grams of the granulated catalyst containing 3% of palladium and 0.6% of rhenium are introduced into an autoclave, together with a solution of 22.8 g of glycolic acid in 100 ml of dioxan. Hydrogen is added (150 bars), and the mixture is heated to 145° C. After a period of 1.5 hours the reaction is discontinued, and the catalyst is filtered off. 118.3 Grams of reaction solution are obtained which contain 16.9 g of ethylene glycol.

EXAMPLE 16

15 Grams of kieselguhr are mixed with a solution of 2.2 g of rhenium heptoxide and 0.47 g of palladium-(II) acetate in 50 ml of acetic acid, and the mixture is dried in the rotary evaporator at 60° C. in the water jet vacuum. Subsequently said mixture is heated to 100° C. in a tube furnace under 12 Nl of nitrogen per hour, and 1 Nl of hydrogen is added to the nitrogen per hour. The mixture is heated to 200° C. within 4 hours, the nitrogen is replaced by hydrogen (15 Nl/h), and subsequently the mixture is reduced for 3 hours at 250° C.

A solution of 15 g of glycolic acid in 100 ml of dioxan is introduced, together with 5 g of the catalyst containing 10% of rhenium and 0.1% of palladium, into a 1 liter shaking autoclave.

Hydrogen is added (185 bars), then the mixture is heated to 241° C., and the reaction is allowed to take place at this temperature for about 4 hours.

After this time the process is discontinued. 111 Grams of a water-clear reaction solution are obtained which contain 9.9 g (80% of the theory) of glycolic acid.

What is claimed is:

1. A process for the preparation of ethylene glycol from glycolic acid, which comprises reacting a solution consisting essentially of glycolic acid, or, glycolic acid and a solvent selected from the group consisting of cyclic ethers, open-chain ethers and water, with hydrogen in the presence of a hydrogenation catalyst which consists essentially of a platinum metal of group VIII and/or a compound thereof in admixture with either
   1. an element of group VIIb and/or a compound thereof, or
   2. gold or silver and/or a compound thereof, or
   3. an element of group VIIb and/or a compound thereof as well as gold or silver and/or a compound thereof.

2. A process as claimed in claim 1, which comprises using as component of group VIIb rhenium or one of its compounds, as platinum metal component of group VIII ruthenium, palladium or platinum or one of the compounds thereof, and as component of group Ib gold or silver or one of the compounds thereof.

3. A process as claimed in claim 1 or 2, wherein the catalyst contains as component of group VIIb rhenium or one of its compounds, as component of group Ib silver or one of its compounds, and as component of group VIII palladium or one of its compounds.

4. A process as claimed in claim 1 or 2, which comprises using as compounds of the elements of groups VIII, VIIb and Ib the oxides, oxide-hydrates, carboxylates, chelates of 1,3-diketo compounds, nitrates, carbonates or borides.

5. A process as claimed in claim 1, wherein the catalyst is applied onto a carrier.

6. A process as claimed in claim 5, which comprises using as carrier a silicoacetate of a bivalent element.

7. A process as claimed in claim 6, which comprises using the silicoacetate of magnesium, calcium, nickel, cobalt, zinc, cadmium, strontium or manganese.

8. A process as claimed in claim 6, which comprises preparing the silicoacetate carrier by treating a metal silicate with acetic acid.

9. A process as claimed in claim 1, wherein the reaction temperature is in the range of from 50° to 300° C.

10. A process as claimed in claim 1, wherein the reaction pressure is in the range of from 50 to 500 bars.

11. A process as claimed in claim 5, which comprises applying the catalytically active component of the hydrogenation catalyst as solutions in carboxylic acid, water, acetone, methanol or methylene chloride ($CH_2Cl_2$).

12. A process as claimed in claim 1, which comprises applying the catalytically active components in an acetic solution onto a carrier, then removing the acetic acid by drying at elevated temperatures in vacuo or at normal pressure, and subsequently treating the catalyst in the gas or liquid phase at a temperature in the range of from 15° to 200° C. with reducing agents.

* * * * *